(12) United States Patent
Frederich et al.

(10) Patent No.: US 12,049,449 B2
(45) Date of Patent: Jul. 30, 2024

(54) METHODS OF HYDROMETHYLATION OF ALKENES AND KETONES

(71) Applicant: The Florida State University Research Foundation, Inc., Tallahassee, FL (US)

(72) Inventors: James H. Frederich, Tallahassee, FL (US); James A. Law, Tallahassee, FL (US)

(73) Assignee: The Florida State University Research Foundation, Inc., Tallahassee, FL (US)

( * ) Notice: Subject to any disclaimer, the term of this patent is extended or adjusted under 35 U.S.C. 154(b) by 0 days.

(21) Appl. No.: 17/385,528

(22) Filed: Jul. 26, 2021

(65) Prior Publication Data
US 2023/0069723 A1    Mar. 2, 2023

(51) Int. Cl.
*C07D 211/96*    (2006.01)

(52) U.S. Cl.
CPC ................... *C07D 211/96* (2013.01)

(58) Field of Classification Search
CPC .................................................. C07D 211/96
See application file for complete search history.

(56) References Cited

PUBLICATIONS

Brown-Wensley et al., 55(11) Pure & Appl. Chem., 1733-1744 (1983) (Year: 1983).*
Law, Bartfield, Frederick, 60 Angew. Chem. Int. Ed. 14360-14364 (2021) (Year: 2021).*
Ho et al. "An Alternate Path to Reductive Elimination for Group IVB Metals: Mechanism of Cyclopropane Formation from Titanacyclobutanes", Journal of the American Chemical Society, 1984, 106(5): 1533-1534.
Feng et al., "Late-Stage Oxidative C(sp3)-H Methylation", Nature, 2020, 580, 621-627.
Friis et al. "Cobalt-Catalysed C—H Methylation for Late-Stage Drug Diversification," Nat Chem. 2020, 12(6): 511-519.
Parnes et al. "Alkyl Groups Migration from Tetra-Alkyl-Silanes, -Germanes, and -Stannanes to Carbenium Ions, Effected by Lewis Acids: A Novel Method for Synthesising Hydrocarbons with a Quaternary Carbon Atom", J. Chem. Soc. Chem. Commun. 1980, 16: 748.
Terao et al. "Zirconocene-Catalyzed Alkylation of Aryl Alkenes with Alkyl Tosylates, Sulfates and Bromides", Tetrahedron Letters, 1998, 39(50): 9201-9204.
Fontaine et al. "Control of Selectivity in the Hydromethylation of Olefins via Ligand Modification in Scandocene Catalysts", Organometallics, 2005, 24(18): 4340-4342.
Clausen et al. "Catalytic Protodeboronation of Pinacol Boronic Esters: Formal Anti-Markovnikov Hydromethylation of Alkenes", Chemical Science, 2014, 24: 6210-6214.
Zhu et al. "Photocatalytic Hydromethylation and Hydroalkylation of Olefins Enabled by Titanium Dioxide Mediated Decarboxylation", Journal of the American Chemical Society, 2020, 142(42): 17913-17918.
Negishi et al. "A Quarter of a Century of Explorations in Organozirconium Chemistry," Dalton Transactions, 2005, (5): 827-848.
Van Horn et al. "Controlled Carbometallation : II. The Addition Reaction of Trimethylalane-Titanocene Dichloride with Acetylenes", Journal of Organometallic Chemistry, 1978, 156(1): C20-C24.
McMurray et al. "Stereoselective Total Synthesis of the Complement Inhibitor K-76", Journal of the American Chemical Society, 1985, 107(9): 2712-2720.
Dao et al. "Hydromethylation of Unactivated Olefins", Journal of the American Chemical Society, 2015, 137(25): 8046-8049.
Pine et al. "Carbonyl Methylenation and Alkylidenation Using Titanium-Based Reagents", Organic Reactions, 1993, 43: 1-90.
Salvati et al. "Modular Access to Functionalized 5-8-5 Fused Ring Systems via a Photoinduced Cycloisomerization Reaction", Chemical Science, 2018, 24(9): 5389-5393.
Tebbe et al. "Olefin Homologation with Titanium Methylene Compounds," Journal of the American Chemical Society, 1978, 100(11): 3611-3613.
Tebbe et al. "Titanacyclobutenes", Journal of the American Chemical Society, 1980, 102(19): 6149-6151.
Pine et al. "Titanium-Mediated Methylene-Transfer Reactions. Direct Conversion of Esters into Vinyl Ethers", Journal of the American Chemical Society, 1980, 102(9): 3270-3272.
Ott et al. "1,3-Dimetallacyclobutanes in Metal-Methylidene Dimerization Reactions," Journal of the American Chemical Society, 1981, 103(19): 5922-5923.
Buchwald et al. "A Titanium Vinylidene Route to Substituted Allenes", Journal of the American Chemical Society, 1983, 105(16): 5490-5491.

* cited by examiner

*Primary Examiner* — Timothy R Rozof
(74) *Attorney, Agent, or Firm* — Eversheds Sutherland (US) LLP

(57) ABSTRACT

Methods of hydromethylation of alkenes and ketones, including methods that use Tebbe's reagent. The methods may include contacting $Cp_2Ti(\mu\text{-}Cl)(\mu\text{-}CH_2)AlMe_2$ and an alkene or a ketone to produce an intermediate product that may include a titanacyclobutane. The intermediate product may be contacted with an acid to produce a methylated product.

17 Claims, 1 Drawing Sheet

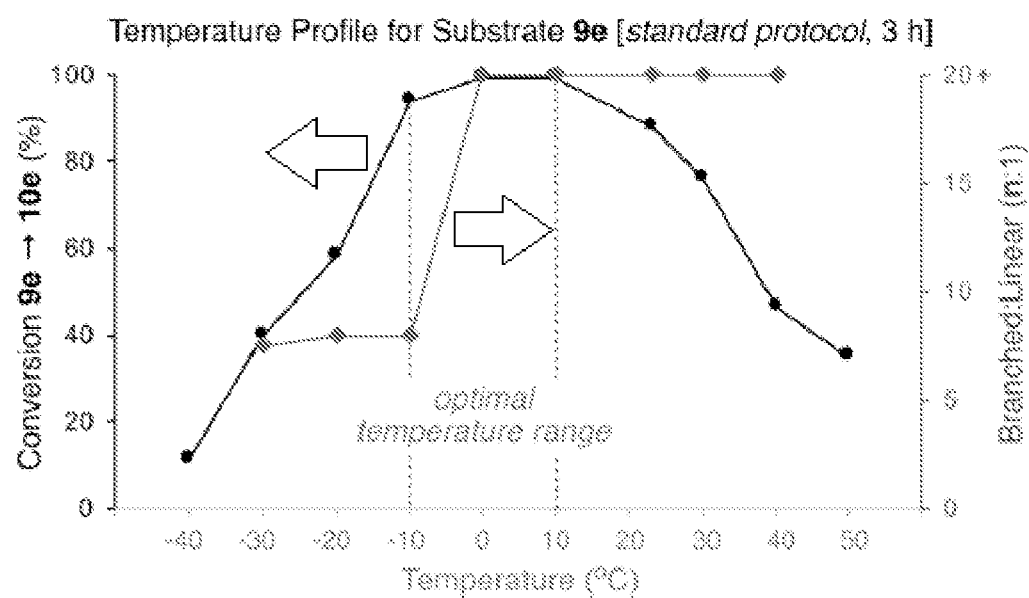

METHODS OF HYDROMETHYLATION OF ALKENES AND KETONES

STATEMENT REGARDING FEDERALLY SPONSORED RESEARCH OR DEVELOPMENT

This invention was made with government support under Contract No. R01GM125926 awarded by the National Institutes of Health. The government has certain rights in this invention.

BACKGROUND

Methyl groups are ubiquitous in biologically active molecules. Site-specific methylation can be a valuable strategy to optimize the pharmacology of bioactive small molecules. This "magic methyl" effect has inspired strategies for selective C—H bond methylation that facilitate the late-stage diversification of complex structures (see, e.g., Feng., K et al. *Nature* 2020, 580, 621-627; and Friis, S. D. et al. *Nat. Chem.* 2020,12, 511-519).

The addition of methane across a C—C π-system may provide an appealing and complementary approach to small-molecule methylation. Despite advances in catalytic alkene hydrofunctionalization, however, there are few direct methods for regioselective hydromethylation (see, e.g., Parnes, Z. N. et al. *J. Chem. Soc. Chem. Commun.* 1980, 748; Terao, J. et al. *Tetrahedron Lett.* 1998, 39, 9201-9204; Fontaine, F. G. et al. Organometallics 2005, 24, 4340-4342; Clausen, F. et al. *Chem. Sci.* 2019, 10, 6210-6214; Zhu, Q. et al. *J. Am. Chem. Soc.* 2020, 142, 17913-17918; Negishi, E. *Dalton Trans.* 2004, 827-848; Van Horn, D. E. et al. *J. Organomet. Chem.* 1978, 156, C20-C24). A procedure using cyclopropanation and reductive C—C bond cleavage has been developed that provides an indirect approach to this problem (see, e.g., McMurry, J. E. et al. *J. Am. Chem. Soc.* 1985, 107, 2712-2720). A more direct approach also has been developed, which is a branch-selective hydromethylation procedure using Fe-mediated hydrogen-atom transfer (see, e.g., Dao, H. T. et al. *J. Am. Chem. Soc.* 2015, 137, 8046-8049).

There remains a need for methods for introducing methyl groups into chemical structures, including polyfunctional structures, with improved efficacy and/or selectivity.

BRIEF SUMMARY

Provided herein are methods of hydromethylation, including methods for the direct Markovnikov hydromethylation of alkenes. In some embodiments, the methods provided herein exploit the degenerate metathesis reaction between the titanium methylidene unveiled from Tebbe's reagent, i.e., $Cp_2Ti(\mu\text{-}Cl)(\mu\text{-}CH_2)AlMe_2$, and unactivated alkenes. Protonolysis of the resulting titanacyclobutanes in situ may effect hydromethylation in a chemo-, regio-, and site-selective manner. The methods provided herein may be applied to a number of chemical structures, such as mono- and di-substituted alkenes containing pendant alcohols, ethers, amides, carbamates, amines, or a combination thereof.

In one aspect, methods of hydromethylation are provided. In some embodiments, the methods include contacting (i) an alkene or a ketone, and (ii) $Cp_2Ti(\mu\text{-}Cl)(\mu\text{-}CH_2)AlMe_2$ to produce an intermediate product; and contacting the intermediate product with an acid to produce a methylated product. The contacting of (i) the alkene or the ketone and (ii) $Cp_2Ti(\mu\text{-}Cl)(\mu\text{-}CH_2)AlMe_2$ may occur in the presence of a Lewis base.

Additional aspects will be set forth in part in the description which follows, and in part will be obvious from the description, or may be learned by practice of the aspects described herein. The advantages described herein may be realized and attained by means of the elements and combinations particularly pointed out in the appended claims. It is to be understood that both the foregoing general description and the following detailed description are exemplary and explanatory only and are not restrictive.

BRIEF DESCRIPTION OF THE DRAWINGS

FIG. 1 depicts a plot of conversion percentage and branched: linear ratios versus temperature for the hydromethylation of an embodiment of an alkene.

DETAILED DESCRIPTION

Provided herein are methods of hydromethylation. In some embodiments, the methods include contacting an alkene $Cp_2Ti(\mu\text{-}Cl)(\mu\text{-}CH_2)AlMe_2$ (i.e., Tebbe's reagent) to produce an intermediate product. In some embodiments, the methods include contacting a ketone and $Cp_2Ti(\mu\text{-}Cl)(\mu\text{-}CH_2)AlMe_2$ to produce an intermediate product. The intermediate product may include a titanacyclobutane moiety, as described herein.

An alkene or ketone may be contacted with any amount of $Cp_2Ti(\mu\text{-}Cl)(\mu\text{-}CH_2)AlMe_2$. In some embodiments, an alkene or ketone is contacted with at least one equivalent of $Cp_2Ti(\mu\text{-}Cl)(\mu\text{-}CH_2)AlMe_2$. For example, the alkene may be contacted with about 1 to about 1.5 equivalents of $Cp_2Ti(\mu\text{-}Cl)(\mu\text{-}CH_2)AlMe_2$. As a further example, a ketone may be contacted with about 2.5 to about 3.5 equivalents of $Cp_2Ti(\mu\text{-}Cl)(\mu\text{-}CH_2)AlMe_2$.

Generally, any ketone may be subjected to the methods described herein. As used herein, the term "ketone" is used to describe any compound that includes a ketone functional group. Functional groups other than ketones may be present in the "ketone" compounds. In some embodiments, the ketone is an acyclic ketone (e.g., methyl ethyl ketone). In some embodiments, the ketone is a cyclic ketone. As used herein, the phrase "cyclic ketone" refers to a ketone in which the carbon atom of the (C=O) moiety is a member of a ring, which may be a heterocyclic ring.

Generally, any alkene may be subjected to the methods described herein. As used herein, the term "alkene" is used to described any compound includes at least one double bond between two carbon atoms. Functional groups other than alkenes may be present in the "alkene" compounds. For example, an alkene may include fusicoccane or a derivative thereof. In some embodiments, an alkene subjected to the methods described herein has a structure according to the following formula (I):

formula (I)

wherein $R^1$, $R^2$, and $R^3$ are independently selected from the group consisting of hydrogen and a $C_1$-$C_{20}$ hydrocarbyl; and wherein, optionally, any two of $R^1$, $R^2$, and $R^3$ (e.g., $R^1$ and $R^2$, $R^2$ and $R^3$, or $R^1$ and $R^3$) are (i) covalently bonded to each other, and (ii) form a cyclic $C_1$-$C_{20}$ hydrocarbyl. The cyclic $C_1$-$C_{20}$ hydrocarbyl may be a heterocyclic $C_1$-$C_{20}$ hydrocarbyl, as explained herein.

In some embodiments, the methods provided herein are regioselective. In some embodiments, an alkene has a structure according to formula (I), wherein $R^2$ and $R^3$ are hydrogen, and the methylated product includes a mixture of a branched alkane (i.e., a methyl group is added to the carbon atom to which $R^1$ and $R^2$ are bonded) and a linear alkane (i.e., a methyl group is added to the carbon atom to which $R^3$ is bonded). The ratio of branched: linear alkane in the methylated product may be about 3:1 to about 30:1, about 3:1 to about 25:1, or about 6:1 to about 25:1.

In some embodiments, at least one of $R^1$, $R^2$, and $R^3$ is hydrogen. For example, $R^1$ may be a hydrogen, and $R^2$ and $R^3$ are independently selected from a $C_1$-$C_{20}$ hydrocarbyl. As a further example, $R^3$ may be a hydrogen, and $R^1$ and $R^2$ are independently selected from a $C_1$-$C_{20}$ hydrocarbyl. In some embodiments, none of $R^1$, $R^2$, and $R^3$ is hydrogen; in other words, the alkene is "tri-substituted", because each of $R^1$, $R^2$, and $R^3$ is independently selected from a $C_1$-$C_{20}$ hydrocarbyl.

In some embodiments, the alkene is an exocyclic alkene. As used herein, the phrase "exocyclic alkene" refers to an alkene in which only one carbon atom of the C=C moiety is a member of a ring, which may be a heterocyclic ring. For example, an exocyclic alkene may be an alkene of formula (I) when $R^1$ and $R^2$ are covalently bonded together and form a cyclic moiety, which may be a heterocyclic moiety.

In some embodiments, the alkene is an endocyclic alkene. As used herein, the phrase "endocyclic alkene" refers to an alkene in which both carbon atoms of the C=C moiety are members of the same ring. For example, an endocyclic alkene may be an alkene of formula (I) when $R^1$ and $R^3$ are covalently bonded together and form a cyclic moiety, which may be a heterocyclic moiety.

In some embodiments, the alkene, which may be an exocyclic or endocyclic alkene, is a tri-substituted alkene. For example, a tri-substituted alkene may be an alkene of formula (I) when none of $R^1$, $R^2$, and $R^3$ is hydrogen.

The contacting of (i) the alkene or the ketone and (ii) $Cp_2Ti(\mu\text{-Cl})(\mu\text{-CH}_2)AlMe_2$ may occur in any suitable liquid (e.g., a solvent). In some embodiments, the contacting of (i) the alkene or the ketone and (ii) $Cp_2Ti(\mu\text{-Cl})(\mu\text{-CH}_2)AlMe_2$ occurs in the presence of a Lewis base. The Lewis base may be a solvent. Any Lewis base capable of facilitating the reactions described herein may be used. In some embodiments, the Lewis base is selected from the group consisting of 4-dimethylaminopyridine and tetahydrofuran. The Lewis base may be used in any amount. In some embodiments, the Lewis base is present at an amount equal to about 0.8 to about 1.2 equivalents of the alkene or ketone.

The contacting of (i) the alkene or the ketone and (ii) $Cp_2Ti(\mu\text{-Cl})(\mu\text{-CH}_2)AlMe_2$ may occur at any temperature and/or pressure. In some embodiments, the temperature is less than 30° C. In some embodiments, the contacting of (i) the alkene or the ketone and (ii) $Cp_2Ti(\mu\text{-Cl})(\mu\text{-CH}_2)AlMe_2$ occurs at a temperature of about −10° C. to about 10° C. In some embodiments, the contacting of (i) the alkene or the ketone and (ii) $Cp_2Ti(\mu\text{-Cl})(\mu\text{-CH}_2)AlMe_2$ occurs under an inert gas.

The methods described herein also may include contacting an intermediate product with an acid to produce a methylated product. As used herein, the phrase "methylated product" refers to a product that includes an alkane formed by substituting at least one methyl group on (i) at least one of the carbon atoms of an alkene functional group of a starting material, or (ii) the carbon atom of a ketone functional group of a starting material. The acid may include any acid capable of facilitating protonolysis of an intermediate product. In some embodiments, the acid is selected from the group consisting of a hydrogen halide, such as hydrogen chloride, and a trihaloacetic acid, such as trifluoroacetic acid.

When used herein with regard to the selection of a substituent, the term "independently" indicates that two differently labeled substituents selected from the same pool of substituents may be the same or different (e.g., $R^1$ and $R^2$ of a molecule may both be selected from "a $C_1$-$C_{20}$ hydrocarbyl", and the $C_1$-$C_{20}$ hydrocarbyls selected for $R^1$ and $R^2$ may be the same or different).

The phrases "$C_1$-$C_{20}$ hydrocarbyl," and the like, as used herein, generally refer to aliphatic, aryl, or arylalkyl groups containing 1 to 20 carbon atoms. Examples of aliphatic groups, in each instance, include, but are not limited to, an alkyl group, a cycloalkyl group, an alkenyl group, a cycloalkenyl group, an alkynyl group, an alkadienyl group, a cyclic group, and the like, and includes all substituted, unsubstituted, branched, and linear analogs or derivatives thereof, in each instance having 1 to about 20 carbon atoms. Examples of alkyl groups include, but are not limited to, methyl, ethyl, propyl, isopropyl, n-butyl, t-butyl, isobutyl, pentyl, hexyl, isohexyl, heptyl, 4,4-dimethylpentyl, octyl, 2,2,4-trimethylpentyl, nonyl, decyl, undecyl and dodecyl. Cycloalkyl moieties may be monocyclic or multicyclic, and examples include cyclopropyl, cyclobutyl, cyclopentyl, cyclohexyl, and adamantyl. Additional examples of alkyl moieties have linear, branched and/or cyclic portions (e.g., 1-ethyl-4-methyl-cyclohexyl). Representative alkenyl moieties include vinyl, allyl, 1-butenyl, 2-butenyl, isobutylenyl, 1-pentenyl, 2-pentenyl, 3-methyl-1-butenyl, 2-methyl-2-butenyl, 2,3-dimethyl-2-butenyl, 1-hexenyl, 2-hexenyl, 3-hexenyl, 1-heptenyl, 2-heptenyl, 3-heptenyl, 1-octenyl, 2-octenyl, 3-octenyl, 1-nonenyl, 2-nonenyl, 3-nonenyl, 1-decenyl, 2-decenyl and 3-decenyl. Representative alkynyl moieties include acetylenyl, propynyl, 1-butynyl, 2-butynyl, 1-pentynyl, 2-pentynyl, 3-methyl-1-butynyl, 4-pentynyl, 1-hexynyl, 2-hexynyl, 5-hexynyl, 1-heptynyl, 2-heptynyl, 6-heptynyl, 1-octynyl, 2-octynyl, 7-octynyl, 1-nonynyl, 2-nonynyl, 8-nonynyl, 1-decynyl, 2-decynyl and 9-decynyl. Examples of aryl or arylalkyl moieties include, but are not limited to, anthracenyl, azulenyl, biphenyl, fluorenyl, indan, indenyl, naphthyl, phenanthrenyl, phenyl, 1,2,3,4-tetrahydro-naphthalene, tolyl, xylyl, mesityl, benzyl, and the like, including any heteroatom substituted derivative thereof.

Unless otherwise indicated, the term "substituted," when used to describe a chemical structure or moiety, refers to a derivative of that structure or moiety wherein (i) a multi-valent non-carbon atom (e.g., oxygen, nitrogen, sulfur, phosphorus, etc.) is bonded to one or more carbon atoms of the chemical structure or moiety (e.g., a "substituted" $C_4$ hydrocarbyl may include, but is not limited to, diethyl ether moiety, a methyl propionate moiety, an N,N-dimethylacetamide moiety, a butoxy moiety, etc., and a "substituted" aryl $C_{12}$ hydrocarbyl may include, but is not limited to, an oxydibenzene moiety, a benzophenone moiety, etc.) or (ii) one or more of its hydrogen atoms (e.g., chlorobenzene may be characterized generally as an aryl $C_6$ hydrocarbyl "substituted" with a chlorine atom) is substituted with a chemical moiety or functional group such as alcohol, alkoxy, alkanoyloxy, alkoxycarbonyl, alkenyl, alkyl (e.g., methyl, ethyl, propyl, t-butyl), alkynyl, alkylcarbonyloxy (—OC(O)alkyl), amide (—C(O)NH-alkyl-or-alkylNHC(O)alkyl), tertiary amine (such as alkylamino, arylamino, arylalkylamino), aryl, aryloxy, azo, carbamoyl (—NHC(O)O-alkyl- or —OC(O)NH-alkyl), carbamyl (e.g., CONH$_2$, as well as CONH-alkyl, CONH-aryl, and CONH-arylalkyl), carboxyl, carboxylic acid, cyano, ester, ether (e.g., methoxy, ethoxy), halo, haloalkyl (e.g., —CCl$_3$, —CF$_3$, —C(CF$_3$)$_3$), heteroalkyl, isocyanate, isothiocyanate, nitrile, nitro, oxo, phosphodiester, sulfide, sulfonamido (e.g., SO$_2$NH$_2$), sulfone, sulfonyl (including alkylsulfonyl, arylsulfonyl and arylalkylsulfonyl), sulfoxide, thiol (e.g., sulfhydryl, thioether) or urea (—NHCONH-alkyl-).

All referenced publications are incorporated herein by reference in their entirety. Furthermore, where a definition or use of a term in a reference, which is incorporated by reference herein, is inconsistent or contrary to the definition of that term provided herein, the definition of that term provided herein applies and the definition of that term in the reference does not apply.

While certain aspects of conventional technologies have been discussed to facilitate disclosure of various embodiments, applicants in no way disclaim these technical aspects, and it is contemplated that the present disclosure may encompass one or more of the conventional technical aspects discussed herein.

The present disclosure may address one or more of the problems and deficiencies of known methods and processes. However, it is contemplated that various embodiments may prove useful in addressing other problems and deficiencies in a number of technical areas. Therefore, the present disclosure should not necessarily be construed as limited to addressing any of the particular problems or deficiencies discussed herein.

In this specification, where a document, act or item of knowledge is referred to or discussed, this reference or discussion is not an admission that the document, act or item of knowledge or any combination thereof was at the priority date, publicly available, known to the public, part of common general knowledge, or otherwise constitutes prior art under the applicable statutory provisions; or is known to be relevant to an attempt to solve any problem with which this specification is concerned.

In the descriptions provided herein, the terms "includes," "is," "containing," "having," and "comprises" are used in an open-ended fashion, and thus should be interpreted to mean "including, but not limited to." When methods are claimed or described in terms of "comprising" various steps or components, the devices, systems, or methods can also "consist essentially of" or "consist of" the various steps or components, unless stated otherwise.

The terms "a," "an," and "the" are intended to include plural alternatives, e.g., at least one. For instance, the disclosure of "an alkene", "an acid", and the like, is meant to encompass one, or mixtures or combinations of more than one alkene, acid, and the like, unless otherwise specified.

Various numerical ranges may be disclosed herein. When Applicant discloses or claims a range of any type, Applicant's intent is to disclose or claim individually each possible number that such a range could reasonably encompass, including end points of the range as well as any sub-ranges and combinations of sub-ranges encompassed therein, unless otherwise specified. Moreover, all numerical end points of ranges disclosed herein are approximate. As a representative example, Applicant discloses, in some embodiments, that a ketone may be contacted with about 2.5 to about 3.5 equivalents of Cp$_2$Ti(µ-Cl))(µ-CH$_2$)AlMe$_2$. This range should be interpreted as encompassing about 2.5 and 3.5 equivalents, and further encompasses "about" each of 2.6, 2.7, 2.8, 2.9, 3, 3.1, 3.2, 3.3, and 3.4 equivalents, including any ranges and sub-ranges between any of these values.

As used herein, the term "about" means plus or minus 10% of the numerical value of the number with which it is being used.

EXAMPLES

The present invention is further illustrated by the following examples, which are not to be construed in any way as imposing limitations upon the scope thereof. On the contrary, it is to be clearly understood that resort may be had to various other aspects, embodiments, modifications, and equivalents thereof which, after reading the description herein, may suggest themselves to one of ordinary skill in the art without departing from the spirit of the present invention or the scope of the appended claims. Thus, other aspects of this invention will be apparent to those skilled in the art from consideration of the specification and practice of the invention disclosed herein.

Unless otherwise stated, reactions were conducted in oven-dried glassware (140° C.) under an atmosphere of nitrogen gas using anhydrous liquids. Tetrahydrofuran (THF), methylene chloride (CH$_2$C$_{12}$), diethyl ether (Et2O), and toluene (PhMe) were dried by passage through activated alumina using a solvent purification system. PhMe used for the synthesis of Tebbe's reagent 1 was degassed by freeze-pump-thaw cycling. Bis(cyclopentadienyl)titanium dichloride was purchased and stored in a nitrogen glovebox. Solutions of AlMe$_3$ (2.0M, PhMe) were purchased and used as received.

Example 1— Reaction Optimization

This example describes a detailed investigation of reaction conditions, as depicted at Table 1. Reagent 1 was Tebbe's reagent, i.e., Cp$_2$Ti(µ-Cl)(µ-CH$_2$)AlMe$_2$.

TABLE 1

Summary of reaction optimization [a-c]

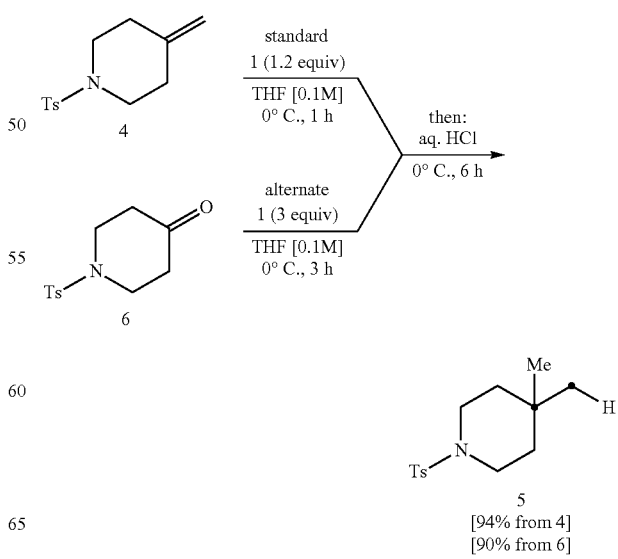

| Entry | Deviation from standard procedure | t[h] | Yield 5 [%] |
|---|---|---|---|
| 1 | PhMe, 1 equiv DMAP | 6 | 16[d] |
| 2 | PhMe | 6 | 0 |
| 3 | PhMe/THF (2:1) | 2 | 80 |
| 4 | none | 1 | 94 |
| 5 | TFA as proton source [e] | 1 | 92 |
| 6 | none, gram scale | 1 | 89 |
| 7 | commercial solution of 1 [f] | 6 | 70[d] |

[a] Yields are based on isolated 5.
[b] Reactions were carried out on a 0.2 mmol scale.
[c] Reagent 1 was prepared directly before use.
[d] Reflects conversion of 4 into 5 as judged by $^1$H NMR spectroscopic analysis of the unpurified reaction mixture.
[e] reaction was treated with TFA at −78° C. and warmed to rt.
[f] Commercial 1 at 0.52$_M$ (in PhMe) was used as received.

As depicted at Table 1, reaction parameters were explored in this example using piperidine 4, which was reacted with a solution of 1 (0.3-0.4M in PhMe) and 4-dimethylamino-pyridine (DMAP) at 0° C. After 6 hours, addition of HCl provided an inseparable mixture of net Markovnikov hydromethylation product 5 (16% conversion) and 4 (entry 1).

No reaction was observed in the absence of a Lewis base (entry 2). In contrast, the reaction was improved using THF as the Lewis base (entry 3), and the best results (94% yield) were obtained using THF as the solvent (entry 4).

It was found that HCl could be replaced by trifluoroacetic acid (TFA) without impacting the reaction efficiency (entry 5). The reaction was executed on a gram scale to give 5 in 89% yield (entry 6). Commercial solutions of 1 (0.5M in PhMe) did not produce comparable results (entry 7). The concentration of 1 was accurate; however, commercial 1 was darker than solutions of 1 freshly prepared from Cp$_2$TiCl$_2$ and AlMe$_3$. The same problem was encountered with prepared solutions of 1 after about 120 hours, which may have suggested the formation of impurities upon storage. It was found that ketone 6 was converted into 5 at 90% yield with 3 equivalents of 1, using otherwise identical conditions. As such, this method also allowed the direct germinal demethylation of ketones.

A series of control reactions was performed, and these reactions demonstrated several properties of the titanacyclobutane 7 formed by the reaction of 1 and 4 (Scheme 1).

Scheme 1. Reactivity of titanacyclobutane 7.

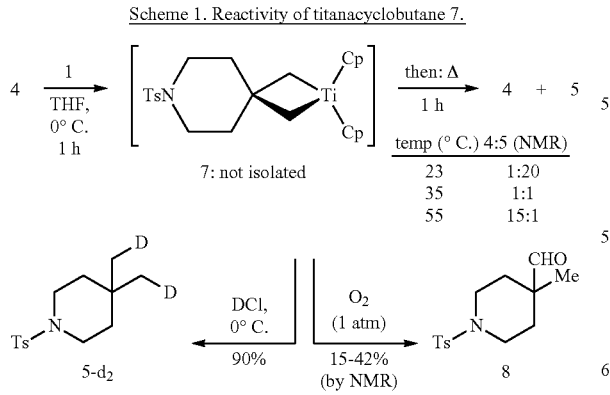

It was unnecessary to isolate this transient species, but it was observed in $^1$H NMR spectra of unpurified reaction mixtures before protonolysis. The thermal stability of 7 was established by forming the metallacycle in situ at 0° C., then warming the reaction for 1 hour before the addition of HCl. This analysis revealed significant cyclo-reversion to 4 after 1 hour at 35° C. (50% by $^1$H NMR spectroscopy).

Conversely, 7 persisted for 10 hours at 0° C. when precautions were taken to exclude air. The introduction of oxygen (1 atm) resulted in the rapid formulation of by-products, the most significant being aldehyde 8. However, when handled as described herein, 7 functioned as a useful 1,3-dianion equivalent. This feature was showcased by the reaction of DCl with 7 at 0° C. to furnish isotopically labeled 5-d$_2$ in 90% yield and with ≥90% deuterium incorporation.

Example 2— Study of Regioselectivity

As depicted at Scheme 2, the regioselectivity of this method was highlighted using α-olefins (9). In principle, both branched (b) and linear (l) hydromethylation isomers of 10 were accessible by protonolysis of titancycles I and II, respectively. However, using the standard procedure, 4-phenyl-1-butene (9a) produced branched alkane 10a (72% yield, >25:1 b/l), which indicated the selective generation of the primary alkyl titanacycle I (see FIG. 1).

Scheme 2. Regioselective hydromethylation of α-olefins.

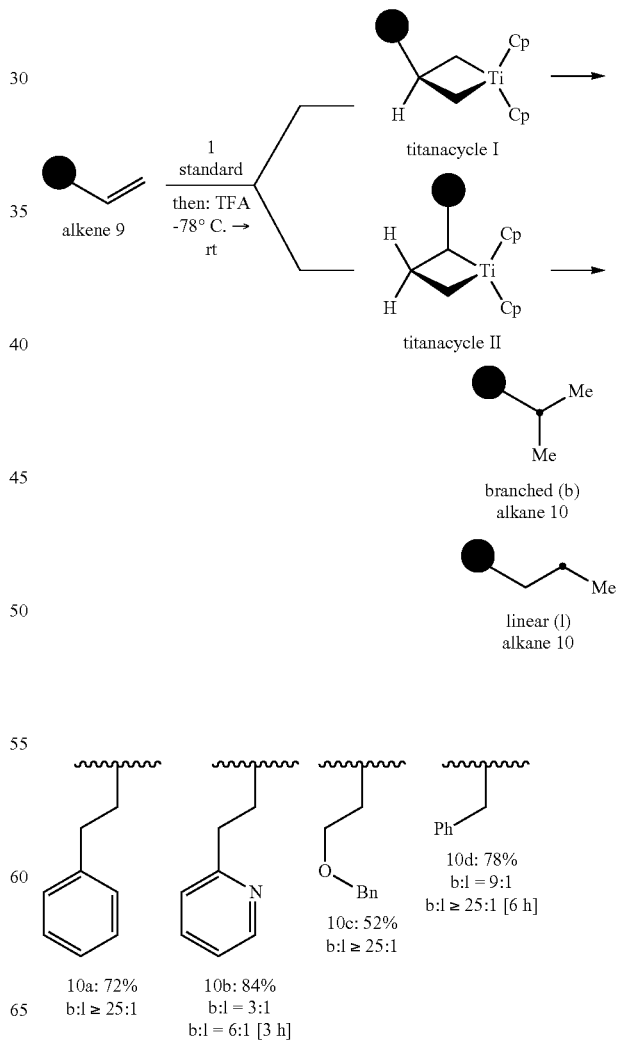

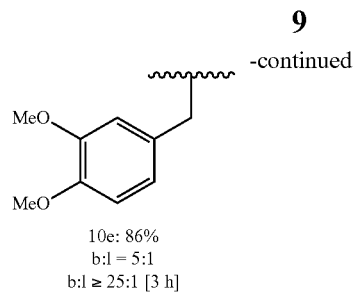

10e: 86%
b:l = 5:1
b:l ≥ 25:1 [3 h]

In comparison, pyridine cogener 9b afforded 10b in 71% yield, but with reduced regioselectivity (3:1 b/1).

In this case, the secondary alkyl titanacycle II was stabilized by coordination to the pendant nitrogen atom through a six-membered chelate. Increasing the reaction time to 3 hours before the addition of acid improved the branched selectivity (10b, 3:1→6:1 b/l), which suggested that intermediates I and II equilibrated under the reaction conditions. A directing effective was not observed using homoallylic ether 9c, as shown by the regioselective formation of 10c after 1 hour (52% yield, >25:1 b/l).

In contrast, modest branched selectivity was observed after 1 hour with arene derivatives 9d and 9e. As expected, the regioselectivity in both cases was enhanced to >25:1 by extending the reaction time. This modification allowed 10d and 10e to be isolated in yields of 78% and 85%, respectively.

To interrogate the role of temperature on the formation and equilibrium of titanacyclobutanes I and II, the conversion of methyl eugenol (9e) into products 10e was studied using $^1$H NMR spectroscopy. Therefore, 9e was reacted with 1.2 equivalents 1 in THF (0.1M) for 3 hours at various temperatures, and then treated with TFA at −78° C. These experiments revealed a temperature window of −10° C. to 10° C. to achieve a high conversion into 10e (≥95%). Using these conditions, the regioselectivity (b/1 ratio) improved from 8:1 at −10° C. to >25:1 at 0° C. Taken together, these data demonstrated the role of time and temperature as variables.

Example 3— Hydromethylation of Substituted Alkenes

The hydromethylation of substituted alkenes was explored. As depicted at Scheme 3, alkenes 11 were divided into four groups (I-IV) based on the structure of the titanacyclobutane formed during the reaction.

Scheme 3 general reaction scheme

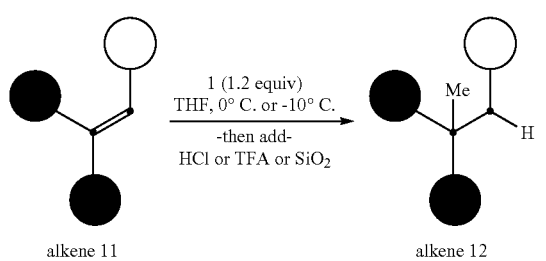

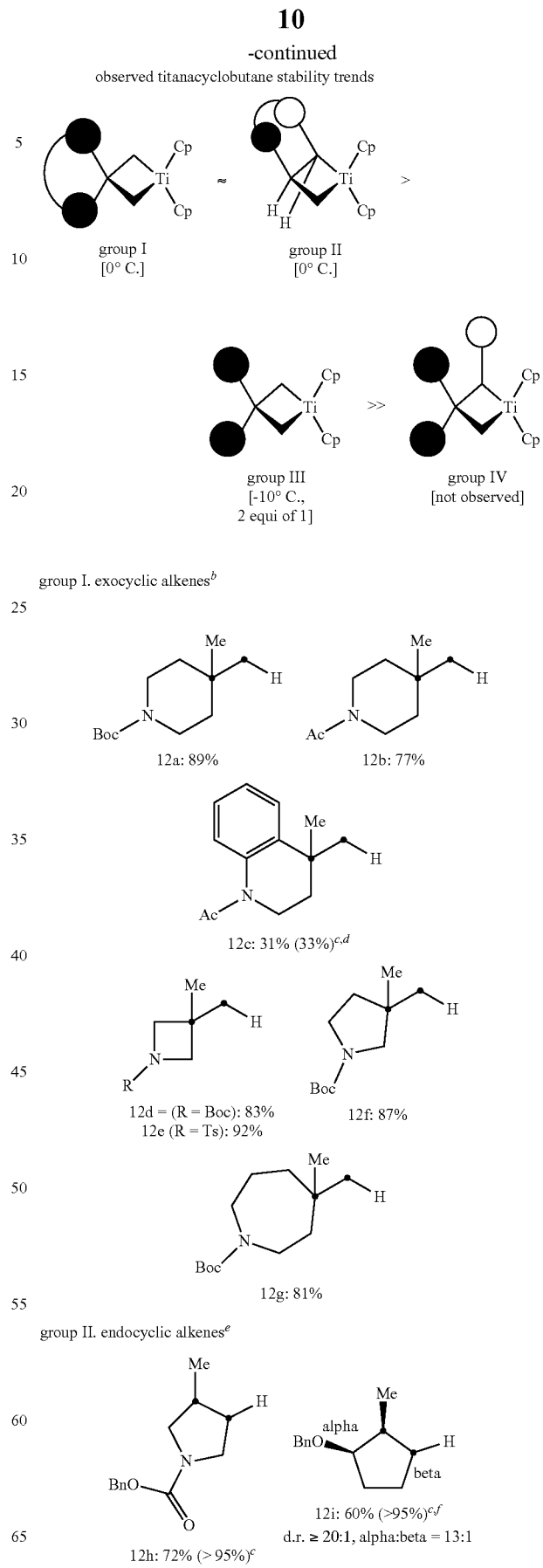

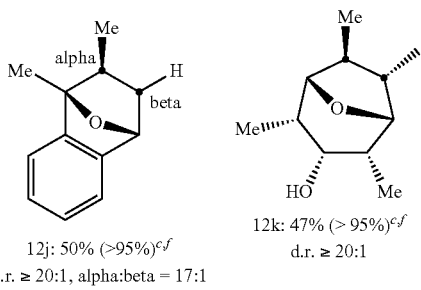

12j: 50% (>95%)[c,f]
d.r. ≥ 20:1, alpha:beta = 17:1

12k: 47% (>95%)[c,f]
d.r. ≥ 20:1 group III. acyclic alkenes[g]

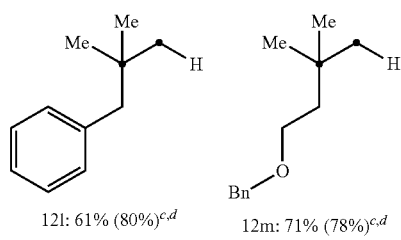

12l: 61% (80%)[c,d]

12m: 71% (78%)[c,d]

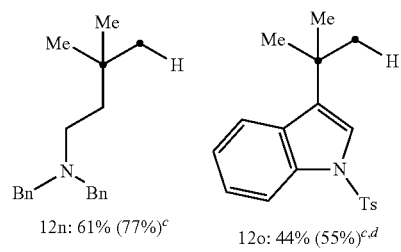

12n: 61% (77%)[c]

12o: 44% (55%)[c,d]

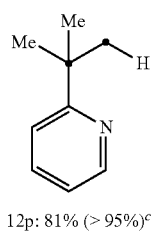

12p: 81% (>95%)[c]

group IV. trisubstituted alkenes

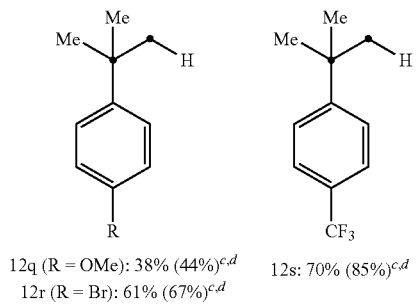

12q (R = OMe): 38% (44%)[c,d]
12r (R = Br): 61% (67%)[c,d]

12s: 70% (85%)[c,d]

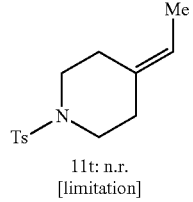

11t: n.r.
[limitation]

Scope and limitations of the titanium-mediated hydromethylation of alkenes.
[a] Yields are based on isolated 12.
[b] Conditions: 1.2 equiv 1, 1 h; 3$_M$ aq HCl, 0° C., 6 h.
[c] Conversion of 11 into 12 as judged by $^1$H NMR spectroscopic analysis of the unpurified reaction mixture.
[d] Unreacted 11 was removed by treating the mixture of 11 and 12 with meta-chloroperoxybenzoic acid (m-CPBA). [25]
[e] Conditions: 1.2 equiv1, 3 h; TFA, -78° C. → rt, 6 h.
[f] SiO$_2$ in EtOAc used in place of TFA.
[g] Conditions: 2 equiv 1, THF (0.1 M), -10° C., 3 h; TFA, -78° C. → rt, 6 h.

Group I included exocyclic 1,1-disubstitutted alkenes derived from nitrogen heterocycles (11a-g). Substrates of this type reacted at 0° C. to afford branched products exclusively. Pendant carbamates (12a) and amides (12b) were tolerated, as were small-(12d-f) and medium-sized (12g) ring systems. In contrast, hydroquinoline 11e reacted slowly under the standard conditions, presumably because the resultant titanacyclobutane was more sterically hindered.

Group II consisted of endocylic 1,2-disubstituted alkenes (11h-k), which reacted at 0° C. in an identical fashion to Group I. Similarly, heterocyclic carbamates (12h), ethers, and alcohols (12i-k) were tolerated. It was observed that the methyl group was selectively delivered to the more congested position (a) within 12i and 12j. This outcome was consistent with a requirement to place the titanium atom in the least sterically encumbered position.

In comparison, branched acyclic alkenes in Group III (11l-s) were less reactive, requiring an excess of 1 (2 equivalents) and longer reaction times (3 hours, -10° C.) to obtain useful results. Nevertheless, 1,1-disubstituted alkyl (11l-n) and (hetero)aryl(11o-s)alkenes were transformed to branched alkanes 12l-s in reasonable yield.

Alkanes 12q-s derived from α-methylstyrene derivatives were noteworthy, as this alkene class was a limitation of the Baran hydromethylation (Dao, H. T. et al. *J. Am. Chem. Soc.* 2015, 137, 8046-8049). Conversely, trisubstituted alkenes (e.g., 11t) were unreactive. In addition, reactions of substrates bearing pendent aldehydes, ketones, or esters were complicated by competitive carbonyl methylenation.

The foregoing differences in alkene reactivity were exploited to achieve site-specific hydromethylation (Scheme 4).

Scheme 4. Site-specific hydromethylation.

a. trisubstituted vs. branches acyclic

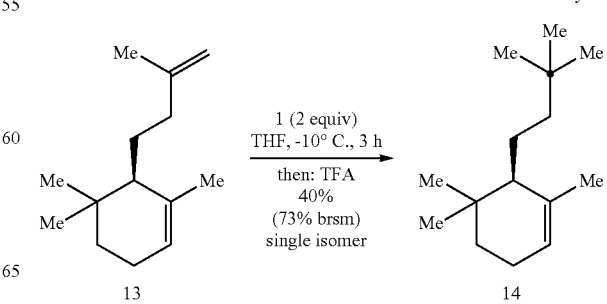

13    14

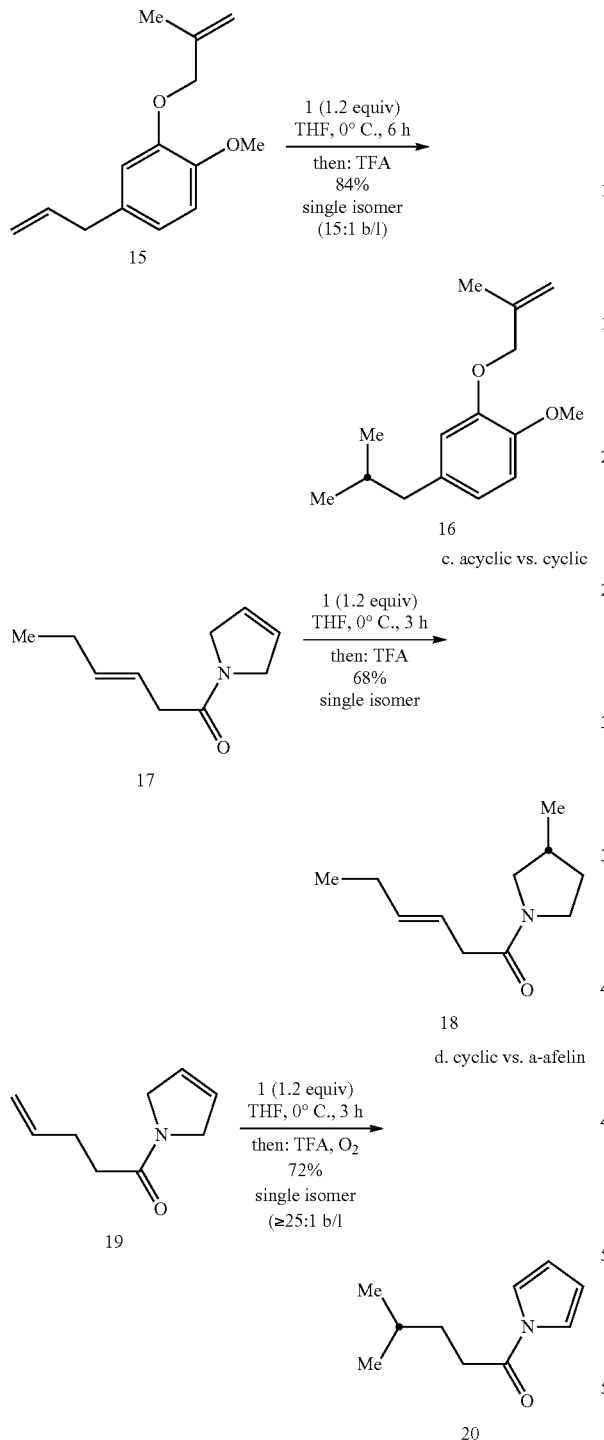

In this example, the acyclic alkene in 13 reacted selectively to give 14 exclusively. Also observed was complete selectivity for the α-olefin in 15 to afford 16 in 84% yield. Likewise, the cyclic alkene of 17 was functionalized, leaving the branched acyclic alkene untouched en route to amide 18. In contrast, the α-olefin of 19 reacted preferentially to give pyrrole 20 in 72% yield following oxidation of the pyrroline ring during purification. These competition experiments suggested the following order or alkene reactivity: α-olefines>cyclic alkenes>acyclic branched alkenes>tri-substituted alkenes.

The invention claimed is:
1. A method of hydromethylation, the method comprising:
contacting (i) an alkene, and (ii) $Cp_2Ti(\mu\text{-}Cl)(\mu\text{-}CH_2)AlMe_2$ to produce an intermediate product in a reaction mixture; and
contacting the intermediate product with an acid to produce a methylated product, wherein the intermediate product is not isolated from the reaction mixture prior to the contacting of the intermediate product with the acid;
wherein the alkene has a structure according to formula (I)—

$$\underset{R^2}{\overset{R^1}{\diagdown}}C=C\overset{R^3}{\diagup};\quad\text{formula (I)}$$

wherein $R^1$ is a $C_1$-$C_{20}$ hydrocarbyl, and $R^2$ and $R^3$ are hydrogen,
wherein the methylated product includes (i) a first product in which the carbon atom bonded to $R^1$ and $R^2$ is methylated, and (ii) a second product in which the carbon atom bonded to $R^3$ is methylated, and
wherein a mole ratio of the first product to the second product is about 3:1 to about 30:1.

2. The method of claim 1, wherein the contacting of (i) the alkene and (ii) $Cp_2Ti(\mu\text{-}Cl)(\mu\text{-}CH_2)AlMe_2$ occurs in the presence of a Lewis base.

3. The method of claim 2, wherein the Lewis base is selected from the group consisting of 4-dimethylaminopyridine and tetrahydrofuran.

4. The method of claim 2, wherein, relative to the alkene, the Lewis base is present at an amount equal to about 0.8 equivalents to about 1.2 equivalents.

5. The method of claim 1, wherein the alkene is contacted with about 1 equivalent to about 1.5 equivalents of the $Cp_2Ti(\mu\text{-}Cl)(\mu\text{-}CH_2)AlMe_2$.

6. The method of claim 1, wherein the alkene is an exocyclic alkene or an endocyclic alkene.

7. The method of claim 6, wherein the exocyclic alkene or the endocyclic alkene is tri-substituted.

8. The method of claim 1, wherein the acid is selected from the group consisting of a hydrogen halide and a trihaloacetic acid.

9. The method of claim 1, wherein the contacting of (i) the alkene and (ii) $Cp_2Ti(\mu\text{-}Cl)(\mu\text{-}CH_2)AlMe_2$ occurs at a temperature less than 30° C.

10. The method of claim 1, wherein the contacting of (i) the alkene and (ii) $Cp_2Ti(\mu\text{-}Cl)(\mu\text{-}CH_2)AlMe_2$ occurs at a temperature of about −10° C. to about 10° C.

11. The method of claim 1, wherein the contacting of (i) the alkene and (ii) $Cp_2Ti(\mu\text{-}Cl)(\mu\text{-}CH_2)AlMe_2$ occurs under an inert gas.

12. A method of hydromethylation, the method comprising:
contacting (i) an alkene, and (ii) $Cp_2Ti(\mu\text{-}Cl)(\mu\text{-}CH_2)AlMe_2$ at a temperature less than 30° C. in the presence of a Lewis base to produce an intermediate product in a reaction mixture, the intermediate product comprising a titanacyclobutane moiety; and contacting the intermediate product with an acid to produce a methylated product, wherein the intermediate product is not isolated from the reaction mixture prior to the contacting of the intermediate product with the acid;

wherein the alkene has a structure according to formula (I)—

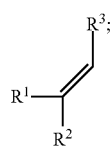

formula (I)

wherein $R^1$ is a $C_1$-$C_{20}$ hydrocarbyl, and $R^2$ and $R^3$ are hydrogen, wherein the methylated product includes (i) a first product in which the carbon atom bonded to $R^1$ and $R^2$ is methylated, and (ii) a second product in which the carbon atom bonded to $R^3$ is methylated, and wherein a mole ratio of the first product to the second product is about 3:1 to about 30:1.

13. The method of claim 12, wherein the Lewis base is selected from the group consisting of 4-dimethylaminopyridine and tetahydrofuran.

14. The method of claim 12, wherein the mole ratio of the first product to the second product is about 6:1 to about 25:1.

15. The method of claim 1, wherein the mole ratio of the first product to the second product is about 6:1 to about 25:1.

16. The method of claim 1, wherein $R^1$ is selected from the group consisting of—

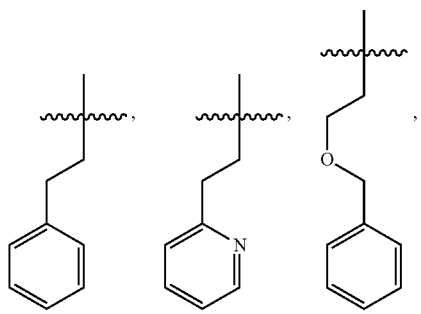

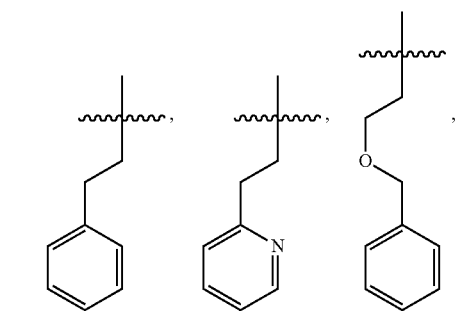

17. The method of claim 12, wherein $R^1$ is selected from the group consisting of—

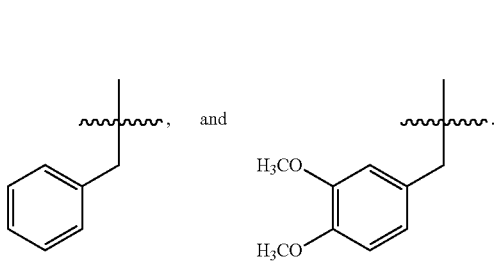

* * * * *